United States Patent [19]

Broger et al.

[11] Patent Number: 5,600,015
[45] Date of Patent: Feb. 4, 1997

[54] ASSYMETRIC HYDROGENATION OF ISOPRENE DERIVATIVES

[75] Inventors: Emil A. Broger, Magden; Robert K. Müller, Basle, both of Switzerland

[73] Assignee: Hoffmann-La Roche Inc., Nutley, N.J.

[21] Appl. No.: 445,068

[22] Filed: May 19, 1995

Related U.S. Application Data

[63] Continuation of Ser. No. 203,859, Mar. 1, 1994, abandoned, which is a continuation of Ser. No. 44,519, Apr. 8, 1993, abandoned.

[30] Foreign Application Priority Data

Apr. 16, 1992 [CH]  Switzerland ............................ 1270/92

[51] Int. Cl.$^6$ .................................................. C07C 45/62
[52] U.S. Cl. ...................... 568/396; 568/596; 568/875; 568/903
[58] Field of Search .................... 568/396, 546, 568/875, 903

[56] References Cited

U.S. PATENT DOCUMENTS

| | | | |
|---|---|---|---|
| 3,639,439 | 2/1972 | Dewhirst | 568/396 |
| 4,962,242 | 10/1990 | Yamada et al. | 568/875 |
| 5,132,464 | 7/1992 | Rossiter et al. | 568/396 |

FOREIGN PATENT DOCUMENTS

| | | | |
|---|---|---|---|
| 0034804 | 9/1981 | European Pat. Off. | 568/396 |
| 0039830 | 11/1981 | European Pat. Off. | 568/396 |
| 0398132 | 11/1990 | European Pat. Off. | 568/396 |
| 0397042 | 11/1990 | European Pat. Off. | 568/396 |
| 0409530 | 1/1991 | European Pat. Off. | 568/396 |
| WO9216536 | 11/1992 | WIPO | 568/396 |

OTHER PUBLICATIONS

Inoue et al Chem. Letters, (1985), p. 1007–8.
Broger et al, Chem. Abst, vol. 114, #164,034n (1991).
Ohta et al, J. Org. Chem, vol. 52, pp. 3174–3176 (1987).

*Primary Examiner*—James H. Reamer
*Attorney, Agent, or Firm*—George W. Johnston; Dennis P. Tramaloni; Bruce A. Pokras

[57] ABSTRACT

There is described a process for the manufacture of isoprene derivatives of the general formula

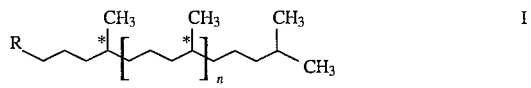

wherein the asymmetric centres can each individually have the (R)- or (S)-configuration, R represents a residue of the formulae

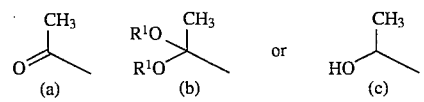

$R^1$ signifies lower alkyl or both $R^1$'s together signify ethylene or propylene and n stands for the number 0, 1 or 2, in which a compound, which is present in the (E)- or (Z)-form, of the general formula

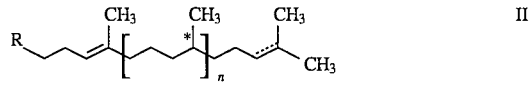

wherein R, n and an optionally present asymmetric centre have the above significance, is asymmetrically hydrogenated with a ruthenium complex of an optically active atropisomeric diphosphine.

32 Claims, No Drawings

ASSYMETRIC HYDROGENATION OF ISOPRENE DERIVATIVES

This is a continuation of application Ser. No. 08/203,859 filed Mar. 1, 1994 now abandoned, which is a continuation of Ser. No. 08/044,519 filed Apr. 8, 1993 now abandoned.

SUMMARY OF THE INVENTION

The present invention is concerned with a novel process for the manufacture of isoprene derivatives of the formula:

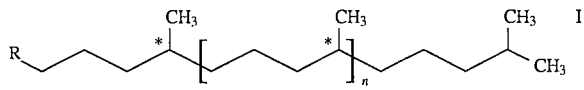

wherein the asymmetric centers each individually can have the (R)- or (S)-configuration, R is a residue of the formula:

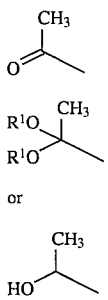

$R^1$ is lower alkyl or both $R^1$'s together are ethylene or propylene and n is 0, 1 or 2,
which process comprises asymmetrically hydrogenating a compound, which is present in the (E)- or (Z)-form, of the formula:

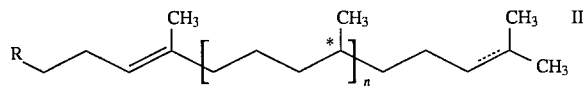

wherein R and n are as above and the dotted line is an optional double bond, in the presence of a ruthenium complex of an optically active atropisomeric diphosphine.

DETAILED DESCRIPTION OF THE INVENTION

The compounds of formula I, above, are known or are to some extent also novel compounds and are suitable intermediates in the synthesis of commercially important compounds such as (R,R,R)-α-tocopherol, vitamin $K_1$ or also phytol and the like.

The compounds of formula II which are used as starting materials are for the most part known compounds. The compounds which are novel can be prepared readily in a manner analogous to the preparation of the known compounds. The starting material of formula II can optionally contain a further double bond as shown by the dotted line in formula II, and this bond is also hydrogenated under the conditions of the asymmetric hydrogenation.

Examples of hydrogenations in the scope of the present invention include the hydrogenation of (R,Z)-6,10,14-trimethylpentadec-5-en-2-one to obtain (R,R)-6, 10-14-trimethylpentadecan-2-one, the hydrogentation of rac.(E)-6,10-dimethylundec-5-en-2-ol to obtain (R)-6,10-dimethylundecan-2-ol, and the hydrogenation of (E)-6,10-dimethyl-2,2-dimethoxy-5-undecene to obtain (R)-6,10-dimethyl-2,2-dimethoxyundecane.

In the preferred embodiment of the invention, (E)- or (Z)-6,10-dimethylundec-5-en-2-one is hydrogenated to obtain (R)- or (S)-6,10-dimethylundecan-2-one.

As ruthenium complexes of atropisomeric diphosphines there especially come into consideration in the scope of the present invention compounds of the formula:

$[RuL]^{2+-l\,(Z)}{}_2$,        III $Ru(Z^1)_2L$        IV or $[Ru(Z^2)_{2-m}(L)(X)](Z^3)m$        V wherein Z is $BF_4^\ominus$, $ClO_4^\ominus$, $B(phenyl)_4^\ominus$ or $PF_6^\ominus$, $Z^1$ is halogen or the group $Y—COO^\ominus$ or $Y—SO_3^\ominus$, Y is lower alkyl, phenyl, halogenated lower alkyl or halogenated phenyl, $Z^2$ is halogen, X is benzene, hexamethylbenzene or p-cymene and m is 1 or 2, $Z^3$ is halogen, $BF_4^\ominus$, $ClO_4^\ominus$ or $B(phenyl)_4^\ominus$ and L is an optically active atropisomeric diphosphine ligand.

As optically active atropisomeric diphosphine ligands there especially come into consideration in the scope of the present invention compounds of the formula in the (R)- or (S)-form:

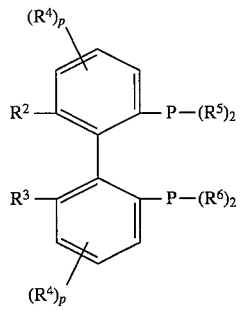

wherein $R^2$ and $R^3$ each independently are lower alkyl, lower alkoxy, hydroxy or protected hydroxy or $R^2$ and $R^3$ together signify $O—CH_2—O—CH_2—O—$, $R^4$ is lower alkyl or lower alkoxy and p is 0, 1 or 2 and $R^5$ and $R^6$ each independently are aryl, a five-membered heteroaromatic group or together with the phosphorous atom a group of the formula:

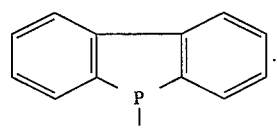

The term "lower alkyl" signifies in the scope of the present invention straight-chain or branched alkyl groups with 1 to 4 carbon atoms such as methyl, ethyl, propyl, isopropyl, n-butyl, isobutyl and tert.butyl. The term "lower alkoxy" signifies groups in which the alkyl residue has the foregoing significance.

As protecting groups for the hydroxy groups there especially come into consideration in the scope of the present invention conventional ether-forming groups such as, e.,g., benzyl, allyl, benzyloxymethyl, lower alkoxymethyl as well as 2-methoxyethoxymethyl and the like.

The term "five-membered heteroaromatic group" stands in the scope of the present invention for a substituent of the formula:

 (a)

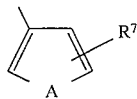 (b)

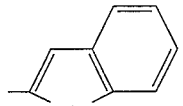 (c)

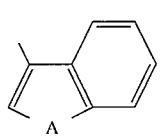 (d)

Furthermore, in the substituents of formulae (a) to (d), A is oxygen, sulphur or $-NR^8$. The substituent $R^7$ is hydrogen, lower alkyl, especially methyl, or lower alkoxy,: especially methoxy, and $R^8$ is for lower alkyl, preferably methyl.

The term "halogen" signifies in the scope of the present invention fluorine, chlorine, bromine or iodine.

The term "halogenated lower alkyl" signifies in the scope of the present invention lower alkyl groups with a variable number of halogen atoms, especially, chlorine or fluorine, whereby preferably at least one halogen atom is situated in the α-position to the —COO⁻group.

Preferred halogenated lower alkyl groups are perfluorinated and perchlorinated lower alkyl groups, for example trifluoromethyl, pentafluoroethyl and the like.

The term "aryl" signifies in the scope of the present invention especially phenyl, which includes unsubstituted phenyl and phenyl substituted in the ortho-, meta- or para-position or also multiply-substituted. As substituents there come-into consideration phenyl, lower alkyl or lower alkoxy groups, preferably methyl or methoxy groups, or also di-lower alkylamino, preferably dimethylamino, groups as well as fluorine, trialkylsilyl such as trimethylsilyl, or also sulphamoyl such as e.,g., N,N-dimethylaminosulphamoyl and the like. Moreover, the term can also signify naphthyl. The term "halogenated phenyl" preferably signifies perfluorophenyl or perfluorobiphenyl.

The notation (*) means that the carbon atom in question is an asymmetric carbon atone.

The diphosphine ligands of formula VI which are used in accordance with the invention are known compounds or analogues of known compounds which can be prepared readily in a manner analogous to the preparation of the known compounds.

In the diphosphine ligands of formula VI, R5 and R6 are preferably the same and are preferably phenyl, furyl, thienyl, 5H-benzo[b]phophindole, or tolyl. The preferred phenyl groups are unsubstituted phenyl, 3,5-di(trimethylsilyl)phenyl, 3,4,5trimethoxyphenyl, p-N,N-dimethylaminosulphamoylphenyl, phenyl-phenyl, and bis-p-(N,N-dimethylamino)phenyl. The preferred furyl groups are 2-furyl, 3-furyl, di-2-benzo[b]furanyl, and bis-5-methylfuran-2-yl.

When R5 and R6 are different, one of those groups is preferably phenyl and the other is preferably thienyl, with unsubstituted phenyl and, 2-thienyl being especially preferred.

In the diphosphine ligands of formula VI, R2 and R3 are preferably the same and are preferably lower alkyl, with methyl being especially preferred, or lower alkoxy, with methoxy being especially preferred. Other preferred groups R2 and R3 are isopropoxy and benzyloxy.

When R2 and R3 are different, one of those groups is preferably isopropoxy and the other is preferably hydroxyl.

In the diphosphine ligands of formula VI, the group(s) R4 is preferably methoxy.

The complexes of formulas IV and V are also known compounds or analogues of known compounds which can be prepared readily in a manner analogous to the preparation of the known compounds, for example, in accordance with EP 397 042.

The complexes of formula III are also known compounds or analogues of known compounds and can be prepared readily in a manner known per se, for example, in accordance with Takaya et al., *J. Org. Chem.*, 1987, 52, 3174–3177.

The asymmetric hydrogenations in accordance with the invention are conveniently effected in an organic solvent which is inert under the reaction conditions. As such solvents there can be mentioned, in particular, lower alcohols such as e.g., methanol, ethanol or trifluoroethanol or mixtures of such alcohols with halogenated hydrocarbons such as methylene chloride, chloroform, hexafluorobenzene and the like or with ethers such as diethyl ether, tetrahydrofuran or dioxan, and the like. Further, ketones such as acetone, diethyl ketone, methyl ethyl ketone etc., esters such as methyl acetate, carboxylic acids such as formic acid, acetic acid and the like, or also water can be can be used.

The ratio of ruthenium to ligand L in the complexes of formulae III, IV and V conveniently lies between about 0.5 and about 2 mol, preferably at about 1 mol, of ruthenium per mol of ligand. The ratio of ruthenium to the substances to be hydrogenated conveniently lies between about 0.01 and about 1 mol%, preferably between about 0.05 and about 0.5 mol %.

The asymmetric hydrogenation with the complexes of formulas III, IV and V is conveniently effected at a temperature of about 0° C. to about 100° C. This hydrogenation is conveniently also effected under pressure, preferably at a pressure of about 5 to about 200 bar, particularly of about 30 to about 100 bar.

In analogy to the use of the optically active atropisomeric ligands of formula VI, there can also be used optically active compounds of the binaphthyl type of the following general formula

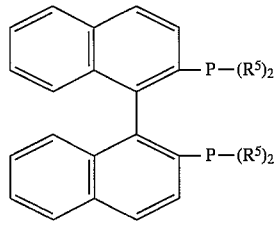

VII wherein $R^5$ and $R^6$ have the same significance as in formula VI. The binaphthyl ring can be substituted in the manner known in the art.

The following Examples serve to illustrate the invention and in no manner represent any limitation. In these Examples the selected abbreviations have the following significance:

GC=capillary gas chromatography e.e.=enantiomeric excess

TLC=thin layer chromatography
RT=room temperature
OAc=acetyl
TFA=trifluoroacetyl
THF=tetrahydrofuran
All temperatures are given in ° Celsius.
2-Furyl-BIPHEMP=(6,6-dimethylbiphenyl-2,2'-diyl)bis(di-2-furylphosphine)
2-Furyl-MeOBIPHEP=(6,6-dimethoxybiphenyl-2,2'-diyl)bis(di-2-furylphosphine
MeOBIPHEP=(6,6'-dimethoxybiphenyl-2,2'-diyl)bis-(diphenylphosphine)
3,5-TMS-MeOBIPHEP=(6,6'-dimethoxybiphenyl-2,2'-diyl)bis {bis-[3,5-di(trimethylsilyl)phenyl]phosphine}
(3,4,5-MeO)-MeOBIPHEP=(6,6'- dimethoxybiphenyl)-2,2'-diyl)bis[bis-(3,4,5-trimethoxyphenyl)phosphine]
p-DMAS-MeOBIPHEP=(6,6'-dimethoxybiphenyl-2,2'-diyl)bis {bis-[p-(N,N-dimethylaminosulphamoyl)phenyl]- phosphine}
2-Thienyl$_2$BIPHEMP=P,P-diphenyl-P',P'-di-2-thienyl-(6,6'-dimethylbiphenyl-2,2'-diyl) diphosphine
BIPHEMP-DIPHOL=5,5'-(6,6'-dimethylbiphenyl-2,2'-diyl)-di-5H-benzo[b]phosphindole
HO/IpropO-BIPHEP=(6-isopropoxy-6'-hydroxybiphenyl-2,2-diyl)bis(diphenylphosphine) IpropO-BIPHEP=(6,6'-diisopropoxybiphenyl-2,2'-diyl)bis-(diphenylphosphine)
p-Biphenyl-MeOBIPHEP=(6,6'-dimethoxybiphenyl-2,2'-diyl)bis(di-4-biphenylylphosphine)
BnO-BIPHEP=(6,6'-dibenzyloxybiphenyl-2,2'-diyl)bis(di-phenylphosphine)
p-DMAPh-MeOBIPHEP=(6,6'-dimethoxybiphenyl-2,2'-diyl)bis {bis-[p-(N,N-dimethylamino)phenyl]phosphine }
p-Anisyl-MeOBIPHEP=(6,6'-dimethoxybiphenyl-2,2'-diyl)bis[di-(p-methoxyphenyl)phosphine ]
2-Thienyl-BIHEMP=(6,6'-dimethylbiphenyl-2,2'-diyl)bis(di-2-thienylphosphine)
2-Thienyl-MeOBIPHEP=(6,6'-dimethoxybiphenyl-2,2'-diyl)bis(di-2-thienylphosphine)
TriMeO-BIPHEP=(4,4'5,5', 6,6'hexamethoxybiphenyl-2,2'-diyl)bis(diphenylphosphine)
BIPHOMP=(5,7-dihydro-dibenz[c,e]oxepin-1,11-diyl)bis-(diphenylphosphine)
p-Tolyl-Me-MeOBIPHEP=(6,6'-dimethoxybiphenyl-2,2'-diyl)bis[di-p-tolylphosphine]
3-Furyl-MeOBIPHEP=(6,6'-dimethoxybiphenyl-2,2'-diyl)bis(di-3-furylphosphine)
Benzofuryl-MeOBIPHEP=(6,6'-methoxybiphenyl-2,2'diyi)-bis-[di-(2-benzo[b]furanyl)phosphine]
MeFuryl-MeOBIPHEP=(6,6'-dimethoxybiphenyl-2,2'-diyl)bis[bis(5-methylfuran-2-yl)phosphine]

EXAMPLE 1 a) 8.33 mg (0.0255 mmol) of di($\eta^2$-acetato)-($\theta^4$-cyclooocta-1,5-diene)ruthenium(II), prepared according to B. Heiser et al., *Tetrahedron: Asymmetry* 2, 51 (1991), and 13.8 mg (0.0255 mmol) of (R)-(6,6'-dimethylbiphenyl-2,2'-diyl) bis(di-2-furylphosphine) were dissolved in 1 ml of methylene chloride and 1 ml of methanol in a glove box (<1 ppm oxygen) and the orange solution was stirred at room temperature for 18 hours. After the addition of 8.9 mg (0.051 mmol) of 50 percent aqueous HBF$_4$ in 0.5 ml of methanol the yellow catalyst solution was stirred for 5 minutes.

b) The glass recipient of a 30 ml autoclave was charged in a glove box with 1.00g (5.09mmol) of (Z)-6,10-dimethylundec-5-en-2-one, 8 ml of methanol and the catalyst solution prepared according to a). The hydrogenation was carried out at 25° and 60 bar of hydrogen for 18 hours. The hydrogenation solution was evaporated on a rotary evaporator at 20° /20mbar, the residue was dissolved in ether and the solution was filtered through a pad of silica gel in order to separate the catalyst. The eluate was evaporated as described above. The residue (0.96 g of yellow oil) consisted of 8.6% educt, 72.9% (R)-6,10-dimethylundecan-2-one and 13.6% of the corresponding dimethyl acetal according to capillary GC. The e.e. of the product was 91.4%. The e.e. determination was carried out according to the method described by A. Knierzinger et al., *Helv. Chim. Acta*, 73, 1087 (1990).

EXAMPLE 2 a) 6.1 mg (0.0188mmol) of di($\eta^2$-acetato)-($\eta^4$-cycloocta-1,5-diene)ruthenium(II) and 10.2 mg (0.0188 mmol) (R)-(6,6'-dimethoxybiphenyl-2,2'-diyl) bis(di-2-furylphosphine) were dissolved in 1 ml of methylene chloride and 1 ml methanol in a glove box (<1 ppm of oxygen) and the orange solution was stirred at room temperature for 18 hours. After the addition of 6.6 mg (0.0375 mmol) of 50 percent aqueous HBF$_4$ in 0.5 ml of methanol the yellow catalyst solution was stirred for 5 minutes.

b) The glass recipient of a 30 ml autoclave was charged in a glove box with 1.00g (3.75 mmol) of (R,Z)-6,10,14-trimethylpentadec-5-en-2-one (95.8% e.e.), 8 ml of methanol and the catalyst solution prepared according to a). The hydrogenation was carried out at 25° and 60 bar of hydrogen for 24 hours. The hydrogenation solution was evaporated on a rotary evaporator at 20° /20mbar and the residue (0.99 g of yellow oil) was chromatographed on 40 g of silica gel; n-hexane-ether 5:1 eluted 873 mg of a colourless oil which consisted of 0.6% educt and 99.2% 6,10,14-trimethylpentadecan-2-one according to capillary GC. The content of (R,R)-6,10-14-trimethylpentadecan-2-one was 93.9% according to the method described by A. Knierzinger et al., *Helv. Chim. Acta*, 73, 1087 (1990) for the determination of the 4 possible isomers (corresponding to 91.2% e.e. with respect to the asymmetric centre C-6).

EXAMPLE 3

A solution of 20.4 mg (0.0255 mmol) of Ru(OAc)$_2$[(S)-MeOBIPHEP](prepared according to B. Heiser et al., *Tetrahedron: Asymmetry*, 2, 51 (1991)) and 8.94 mg (0.0509 mmol) of 50 percent aqueous HBF$_4$ in 4 ml of methanol was stirred for 1 hour. After the addition of 1.01 g (5.09mmol) of rac.(E)-6,10-dimethylundec-5-en-2-ol and a further 5 ml of methanol the hydrogenation was carried out at 25° and 35 bar for 18 hours. The hydrogenation solution was evaporated on a rotary evaporator at 20° /20 mbar, the residue (0.95 g of yellow oil) was dissolved in ether and the solution was filtered through a pad of silica gel. The eluate was evaporated as described above. The residue (670 mg of yellow oil) consisted of 16.8 g educt and 83.2% 6,10- dimethylundecan-2-ol according to capillary GC.

For the e.e. determination, 200 mg of the alcohol were oxidized with 0.3 g of pyridinium chlorochromate in methylene chloride at 25° for 2 hours. From the brown reaction solution there was obtained after filtration through silica gel 0.19 g of a colourless oil which contained 75.9% (R)-6,10-dimethylundecan-2-ol of 74.1% e.e. according to GC.

EXAMPLE 4

A solution of 20.4 mg (0.0255 mmol) of $Ru(OAc)_2[(S)$-MeOBIPHEP]and 5.33 mg (0.028 mmol) of $HBF_4$-diethyl ether complex (Aldrich) in 4 ml of methanol was stirred for 1 hour. After the addition of 1.23 g (5.09mmol) of (E)-6,10-dimethyl-2,2-dimethoxy-5-undecene a further 5 ml of methanol the hydrogenation was carried out at 25° and 35 bar for 18 hours. The hydrogenation solution was evaporated on a rotary evaporator at 20° /20 mbar, the residue (0.98 g of yellow oil) was dissolved in ether and the solution was filtered through a pad of silica gel. The eluate was evaporated as above. The residue (790mg of yellow oil) consisted of 51% educt and 37% (R)-6,10-dimethyl-2,2-dimethoxyundecane 70,4% e.e. according to capillary GC. The e.e. value was carried out in the manner described for the corresponding ketone in Example 1.

EXAMPLES 5–21

Further hydrogenations were carried out in an analogous manner to Example 1 and the results are shown in Table 1.

TABLE 1

Hydrogenation of (E)- or (Z)-6,10-dimethylundec-5-en-2-one with [Ru(MeOBIPHEP)](Z)$_2$ as the catalyst[a]

| Ex. | Educt | Z | MeOBIPHEP config. | S/C [b] | Solvent (ml) | P bar | T °C. | Conversion %[c] | Selectivity %[d] | e.e. %[e] | config. |
|---|---|---|---|---|---|---|---|---|---|---|---|
| 5 | E | BF$_4$ | S | 200 | MeOH (10) | 35 | 25 | 93 | 95 | 77.0 | R |
| 6 | E | BF$_4$ | S | 200 | MeOH (10) | 60 | 25 | 93 | 93 | 80.4 | R |
| 7 | Z | ClO$_4$[f] | S | 200 | MeOH (9), CH$_2$Cl$_2$ (1) | 60 | 25 | 65 | 95 | 73.1 | R |
| 8 | E | BF$_4$ | S | 200 | MeOH (9), CH$_2$Cl$_2$ (1) | 60 | 25 | 94 | 94 | 78.7 | R |
| 9 | Z | BF$_4$ | R | 200 | MeOH (0.5), CHCl$_3$ (9.5) | 60 | 25 | 82 | 98 | 74.4 | R |
| 10 | Z | BF$_4$ | R | 200 | MeOH (0.5), AcOH (9.5) | 60 | 25 | 33 | 79 | 75.0 | R |
| 11 | Z | BF$_4$ | R | 200 | MeOH (0.5), Aceton (9.5) | 60 | 25 | 69 | 97 | 73.3 | R |
| 12 | E | BF$_4$ | S | 200 | MeOH (0.5), THF (9.5) | 60 | 25 | 97 | 98 | 81.2 | R |
| 13 | E | BF$_4$ | S | 200 | MeOH (0.5), Et$_2$O (9.5) | 60 | 25 | 95 | 97 | 88.7 | R |
| 14 | Z | BF$_4$ | S | 200 | MeOH (0.5), Et$_2$O (9.5) | 60 | 25 | 96 | 97 | 87.0 | R |
| 15 | Z | BF$_4$ | R | 200 | MeOH (0.5), AcOEt (9.5) | 60 | 25 | 56 | 97 | 85.0 | R |
| 16 | E | BF$_4$ | S | 200 | MeOH (0.5), THF (2.5), Et$_2$O (7) | 60 | 25 | 96 | 97 | 86.6 | R |
| 17 | Z | BF$_4$ | R | 200 | MeOH (0.5), C$_6$F$_6$ (9.5) | 35 | 25 | 96 | 97 | 88.6 | R |
| 18 | E | BF$_4$ | R | 2000 | CF$_3$CH$_2$OH (10) | 60 | 25 | 100 | 97 | 69.0 | S |
| 19 | Z | BF$_4$ | R | 200 | CF$_3$CH$_2$OH (0.5), Et$_2$O (9.5) | 60 | 25 | 100 | 98 | 86.6 | |
| 20 | Z | BF$_4$ | R | 200 | (CF$_3$)$_2$CHOH (2), Et$_2$O (8) | 60 | 25 | 94 | 97 | 82.4 | R |
| 21 | Z | BF$_4$ | S | 200 | CH$_2$Cl$_2$(0.5), Et$_2$O (9.5) | 60 | 80 | 92 | 93 | 77.4 | S |

[a]1 g (E)- or (Z)-ketone in 10 ml of solvent, reaction time 18 h.
[b]Molar ration educt/catalyst
[c]according to GC, 25 m SE 54 column.
[d]in alcoholic solvents the product was present (<20%) as the ketal. Selectivity = product yield (ketone + ketal) with respect to unreacted educt.
[e]GC determination, see Ex. 1.
[f]prepared analogously to Ex. 1a) using 70 percent HClO$_4$.
MeOH = methanol; AcOH acetic acid; Et$_2$O = diethylether, AcOEt = ethylacetate; C$_6$F$_6$ = hexafluorobenzene.

EXAMPLES 22–30

Further hydrogenations were carried out in an analogous manner to Example 1 and the results are shown in Table 2.

TABLE 2

Asymmetric hydrogenation of (E)- or (Z)-6,10-dimethylundec-5-en-2-one in the presence of $Ru(Z^1)_2[(R)$-2-furylMeOBIPHEP] or $\{Ru[(R)$-2-furylMeOBIPHEP]$\}(Z)_2$[a]

| Ex. | Educt | Z | Solvent (ml) | P bar | T °C. | t h | Conversion %[b] | Selectivity %[b] | e.e. %[b] | Config. |
|---|---|---|---|---|---|---|---|---|---|---|
| 22 | E | BF$_4$ | MeOH (9), CH$_2$Cl$_2$ (1) | 35 | 25 | 18 | 64 | 99 | 90.0 | S |
| 23 | E | BF$_4$ | MeOH (9), CH$_2$Cl$_2$ (1) | 60 | 25 | 18 | 84 | 99 | 91.5 | S |
| 24 | Z | BF$_4$ | MeOH (9), CH$_2$Cl$_2$ (1) | 60 | 25 | 18 | 90 | 97 | 91.4 | R |
| 25 | E | BF$_4$ | MeOH (9), CH$_2$Cl$_2$ (1) | 60 | 80 | 6 | 100 | 86 | 84.4 | S |
| 26 | Z | BF$_4$ | MeOH (9), CH$_2$Cl$_2$ (1) | 60 | 80 | 6 | 100 | 89 | 89.2 | R |
| 27 | Z | BF$_4$ | MeOH (0.5), Et$_2$O (9.5) | 60 | 80 | 6 | 100 | 95 | 89.8 | R |
| 28 | Z | BF$_4$ | MeOH (0.5), Et$_2$O (9.5) | 60 | 100 | 6 | 95 | 92 | 83.0 | R |

TABLE 2-continued

Asymmetric hydrogenation of (E)- or (Z)-6,10-dimethylundec-5-en-2-one in the presence of
Ru(Z$^1$)$_2$[(R)-2-furylMeOBIPHEP] or {Ru[(R)-2-furylMeOBIPHEP]}(Z)$_2$[a]

| Ex. | Educt | Z | Solvent (ml) | P bar | T °C. | t h | Conversion %[b] | Selectivity %[b] | e.e. %[b] | Config. |
|---|---|---|---|---|---|---|---|---|---|---|
| 29 | Z | BF$_4$ | MeOH (9), CH$_2$Cl$_2$ (1) | 60 | 0 | 142 | 48 | 93 | 93.4 | R |
| 30 | Z | Z$^1$ TFA[c] | MeOH (9), CH$_2$Cl$_2$ (1) | 60 | 25 | 18 | 35 | 78 | 80.1 | R |

[a] 1 g of educt in 10 ml of solvent; S/C 200.
[b] see Tab. 1.
[c] Ru(TFA)$_2$[(R)-2-furylMeOBIPHEP] was prepared in an analogous manner to Example 1 from [Ru(TFA)$_2$COD]$_2$ [B. Heiser et al. Tetrahedron: Asymmetry 2, 51 (1991)] and (R)-2-furylMeOBiPHEP.

EXAMPLES 31–49

Further hydrogenations were carried out in an analogous manner to Example 1 and the results are in Table 3.

TABLE 3

Asymmetric hydrogenation of (E)- or (Z)-6,10-dimethylundec-5-en-2-one with [RuL]$^{2+}$(Z)$_2$ as the catalyst[a]

| Ex. | Educt | Chiral ligand | Conversion %[a] | Selectivity %[a] | e.e. %[a] | Config. |
|---|---|---|---|---|---|---|
| 31 | Z | (S)-(3,5-TMS)-MeOBIPHEP | 100 | 16[b] | 87.6 | S |
| 32 | Z | (S)-(3,4,5-MeO)-MeOBIPHEP | 100 | 71[b] | 75.4 | S |
| 33 | E | (R)-p-DMAS-McOBIPHEP | 18 | 75[b] | 84.2 | S |
| 34 | E | (R)-(2-Thienyl)$_2$BIPHEMP | 76 | 85 | 70.0 | S |
| 35 | E | (R)-BIPHEMP-DIPHOL | 54 | 89 | 83.1 | S |
| 36 | E | (R)-HO/IpropO-BIPHEP | 100 | 88 | 76.7 | S |
| 37 | E | (R)-IpropO-BIPHEP | 100 | 89 | 73.6 | S |
| 38 | E | (R)-p-BnO-BIPHEP | 89 | 95 | 78.4 | S |
| 39 | E | (R)-p-Biphenyl-MeOBIPHEP | 66 | 92 | 76.2 | S |
| 40 | E | (S)-p-DMAPh-MeOBIPHEP | 100 | 86 | 70.6 | R |
| 41 | E | (R)-Anisyl-MeOBIPHEP | 100 | 73 | 74.6 | S |
| 42 | Z | (S)-2-Thienyl-BIPHEP | 99 | 42[b] | 80.0 | S |
| 43 | Z | (S)-2-Thienyl-BIPHEMP | 98 | 43[b] | 73.6 | S |
| 44 | E | (S)-TriMeO-BIPHEP | 100 | 91 | 78.7 | R |
| 45 | E | (S)-BIPHOMP | 98 | 92 | 81.2 | R |
| 46 | E | (S)-p-Tolyl-MeOBIPHEP | 100 | 90 | 72.1 | R |
| 47 | E | (S)-(3-Furyl)-MeOBIPHEP | 95 | 92 | 74.8 | R |
| 48 | E | (R)-Benzofuryl-MeOBIPHEP | 45 | 98 | 93.3 | S |
| 49 | Z | (R)-MeFuryl-MeOBIPHEP | 97 | 95 | 92.0 | R |

[a] see Tab. 1.
[b] lower selectivity because of over-hydrogenation to the corresponding alcohol.

EXAMPLE 50

The (R)-(6,6'-dimethoxybiphenyl-2,2'-diyl)bis(di-2-furylphosphine) used in accordance with Examples 1 and 2 was prepared as follows:

a) A solution of 0.30 g (0.442 mmol) of (R)-(6,6'-dimethoxy-biphenyl-2,2'-diyl)bis(phosphonic acid diphenyl ester) in 10 ml of tetrahydrofuran was added dropwise at room temperature within 15 minutes to a Grignard solution prepared from 1.5 ml of 2-iodofuran (67% pure) and 0.30g (12.3 mmol) of magnesium shavings in 10 ml of tetrahydrofuran. After completion of the addition the mixture was heated to 40° for 1 hour. For the working-up, the mixture was treated with 50 ml of sat. NH$_4$Cl solution and 50 ml of ethyl acetate, the phases were separated and the organic phase was washed with sat. NaCl solution, dried over MgSO$_4$, filtered and concentrated. The residue was dissolved in the minimal amount of CH$_2$Cl$_2$ and the solution was applied to a column of 50 g of silica gel. Elution with ethyl acetate and then with tetrahydrofuran yielded 0.20 g of a solid which was recrystallized from 10 ml of tert.butyl methyl ether. There was obtained 0.16 g of (R)-(6,6'-dimethoxybiphenyl-2,2'-diyl)bis(di-2-furylphosphine oxide) as yellowish crystals, m.p. 272° (thermoanalysis); [α]$_D^{20}$=+89.6 (c=1.0, CHCl$_3$).

b) A 0.51 four-necked sulphonation flask equipped with a condenser, thermometer, dropping funnel and mechanical stirrer was charged under argon with 2.90g (5.0mmol) of (R)-(6,6'-dimethoxy- biphenyl-2,2'-diyl)bis(di-2-furylphosphine oxide), 10 ml (41.9 mmol) of tributylamine, 60 ml of xylene isomer mixture and 4.0 ml (5.37 g, 39.6 mmol) of trichlorosilane. The milky-white mixture was boiled under reflux for 4 hours, whereby an almost transparent solution resulted. After cooling 100 ml of deoxygenated 30% sodium hydroxide solution were added dropwise while stirring well in such a manner that the internal temperature did not exceed 700 and the mixture was stirred at 70° for a further 1 hour. After the addition of H$_2$O and CH$_2$Cl$_2$ the phases were separated and the organic phase was washed with 2×50 ml of 30% sodium hydroxide solution, H$_2$O, sat. NH$_4$Cl solution and sat. NaCl solution, dried over MgSO$_4$, filtered and evaporated. The white powder obtained (4.40 g) was dissolved in CH$_2$Cl$_2$, the solution was treated with ethanol and the CH$_2$Cl$_2$ was evaporated on a rotary evaporator. The separated solid was filtered off, washed with ethanol and pentane and dried in a high vacuum (~10 Pa) for 1 hour at 100°. There were obtained 2.50g of (R)-(6,6'-dimethoxybiphenyl-2,2'-diyl)bis(di-2-furylphosphine) as yellowish crystals; m.p. 176°; $[\alpha]_D^{20}=+6.9$ (c=1, CHCl$_3$).

The (R)-(6,6'-dimethoxybiphenyl-2,2'-diyl)bis(phosphonic acid diphenyl ester) used as the starting material and, respectively, the corresponding (S) compound were prepared as follows:

a) 76.5 g (0.122mol) of (2-iodo-3-methoxyphenyl)phosphonic acid diphenyl ester (75% pure) and 25.0 g (0.393 mol) of activated copper powder were placed under argon in a 1 l four-necked sulphonation flask equipped with a condenser, thermometer, stirrer and headpiece for inert gas treatment and 200 ml of N,N-dimethylformamide were allowed to flow in. The dark brown suspension was heated to 140° (oil bath temperature) for 1 hour, after which time complete conversion had occurred according to TLC analysis. The cooled reaction mixture was transferred into a round flask with methylene chloride and evaporated to dryness on a rotary evaporator at 70°. The residue was treated with 200ml of methylene chloride, the mixture was stirred well and filtered, and the filter residue was washed with 100 ml of methylene chloride. The filtrate was washed three times with 100 ml of sat. NH$_4$Cl solution, a small amount of solid formed in the first washing operating being filtered off, and subsequently dried over MgSO$_4$, filtered and concentrated. After drying in a high vacuum (~10 Pa) at 80° for 2 hours there were obtained 59.6 g of crude (RS)-(6,6'-dimethoxybiphenyl-2,2'-diyl)bis(phosphonic acid diphenyl ester).

ba) A solution of 59.6 g of the crude diphenyl ester obtained according to a) in 50 ml of dichloromethane was placed in a 1 l round flask and treated with a solution of 35.8 g (0.10 mol) of (-)-O,O'-dibenzoyl-L-tartaric acid in 100 ml of ethyl acetate. The solution was then evaporated on a rotary evaporator at 600 mbar, whereby the CH$_2$Cl$_2$ distilled off and a white solid separated. This was filtered off under suction, washed three times with 20 ml of ethyl acetate and 20 ml of hexane and dried in a high vacuum (~10 Pa). There were obtained 21.8 g of (R)-diphenyl ester/(-)-DBT adduct as a white powder. $[\alpha]_D^{20}=-95.6$ (c=1 in ethanol).

The mother liquors and wash solutions were placed on one side for the preparation of the other enantiomer.

bb) The material obtained according to ba) was stirred with 100 ml of dichloromethane, 50 ml of sat. NaHCO$_3$ solution and 50 ml of deionized water in a 1 l Erlenmeyer with a magnetic stirrer until all of the solid had passed into solution (30 minutes). The phases were separated and the organic phase was washed twice with 100 ml of semi-sat. NaHCO$_3$ solution, 50 ml of deionized water and 50 ml of sat. NaCl solution, dried over MgSO$_4$, filtered and evaporated. The oily residue was treated with 20 ml of tert.-butyl methyl ether, whereby crystallization occurred. After evaporation and drying in a high vacuum (~10 Pa) at 60° for 1 hour there were obtained 13.8 g of (R)-(6,6'-dimethoxy- biphenyl-2,2'-diyl)bis(phosphonic acid diphenyl ester) as white crystals. M.p. 125–125 5°; $[\alpha]_D^{20}=-18.9$ (c=1 in CHCl$_3$).

ca) The mother liquors and wash solutions from ba) were evaporated in a 1 l round flask. The residue was taken up in 100 ml of dichloromethane and the solution was stirred for 30minutes with 50 ml of sat. NaHCO$_3$ solution and 50 ml of deionized water. The phases were separated and the organic phase was washed with 100 ml of semi-sat. NaHCO$_3$ solution, 50 ml of deionized water and 50 ml of sat. NaCl solution, dried over MgSO$_4$, filtered and concentrated. The brown oil obtained was taken up in 50 ml of dichloromethane and the solution was treated with a solution of 18.0 g (0.050mol) of (+)-O,O'-dibenzoyl-D-tartaric acid in 100 ml of ethyl acetate. The solution was then concentrated on a rotary evaporator at 600 mbar, whereby the CH$_2$Cl$_2$ distilled off and a white solid separated. This was filtered off under suction, washed three times with 20 ml of ethyl acetate and 20 ml of hexane and dried in a high vacuum (~10 Pa). There were obtained 22 g of (S)-diphenyl ester/(+)-DBT adduct as a slightly yellowish powder. $[\alpha]_D^{20}=+96$ (c=1 in ethanol).

cb) The material obtained according to ca) was processed as described in bb). There were obtained 13.9 g of (S)-(6, 6'-dimethoxybiphenyl2,2'-diyl)bis(phosphonic acid diphenyl ester) as white crystals. M.p. 124°–125°; $[\alpha]_D^{20}=+18.7$ (c=1 in CHCl$_3$).

d) The (2-iodo-3-methoxyphenyl)phosphonic acid diphenyl ester used as the starting material was prepared as follows:

daa) A suspension of 13.0g (0.535 mol) of magnesium shavings in 50 ml of dry tetrahydrofuran was placed under argon in a 0.5 l four-necked flask equipped with a stirrer, condenser, thermometer and headpiece for inert gas treatment. Thereto there was added dropwise a solution of 93.5 g (0.50 mol) of 3-bromoanisole in 200 ml of dry tetrahydrofuran within 90 minutes in such a manner that the reaction temperature did not exceed 35°. After the addition the mixture was diluted with an additional 150 ml of dry tetrahydrofuran in order to avoid precipitation of the Grignard reagent.

dab) 259.8 g (0.967 mol) of diphenyl chlorophosphate and 200 ml of dry tetrahydrofuran were placed in a 1.5 l four-necked flask equipped with a stirrer, thermometer, head piece for inert gas treatment and CO$_2$/acetone cooling bath and the solution was cooled to –78°. Thereto there was now added dropwise within 2 hours the solution of the Grignard reagent prepared according to baa) in such a manner that the reaction temperature did not exceed –70°. After completion of the addition the mixture was left to warm to room temperature overnight while stirring. The reaction mixture, which contained some fine white precipitate was poured into a mixture of 2 l of ice-water, 2 l of sat. NaHCO$_3$ solution and 1 l of diethyl ether in a 10 l stirring vessel. After vigorous intermixing for 10minutes the aqueous phase was separated and the organic phase was washed in succession with 1 l of sat. NaHCO$_3$ solution, 200ml of 25% ammonia, 100ml of 25% ammonia and three times with 500 ml of sat. NaCl solution. After drying over MgSO$_4$ the solution was evaporated, the residue was taken up in 1 l of diethyl ether and the solution was left to stand at 0° overnight. The white solid (12 g) which thereby separated was removed by filtration and discarded. The filtrate was evaporated, dried in a high vacuum (~10 Pa), the residue obtained (163 g of yellow oil) was taken up in 300 ml of hexane/toluene 1:1 and the solution was filtered over 500 g of silica gel. By elution firstly with 3 l of hexane and 8 l of hexane/ethyl acetate 9:1 and thereafter with 2 l of hexane/ethyl acetate 4:1 and 2 l of hexane/ethyl acetate 7:3 there were obtained, after drying in a high vacuum (10 Pa) at 40° for 1 hour, 118 g of (3-methoxyphenyl)phosphonic acid diphenyl ester as a pale yellowish oil.

db) 300 ml of dry tetrahydrofuran were placed in a 1.5 l four-necked flask equipped with a stirrer, thermometer, headpiece for inert gas treatment, dropping funnel with pressure balance and CO$_2$/acetone cooling bath. Thereto there were added 70 ml (0.412 mol) of 2,2,6,6tetramethylpiperidine by means of a syringe and the solution was cooled to –78°. 210 ml (0.336 mol) of 1.6N butyllithium solution in hexane were filled into the dropping funnel via a steel canula. The butyllithium solution was dropped into the reaction vessel within about 10 minutes, whereby the temperature rose to about −50° and a white precipitate formed. The CO₂/acetone cooling bath was replaced by an ice/ethanol bath and the reaction mixture was stirred at about −150 for 30 minutes, then again cooled to −78°.

250ml of dry tetrahydrofuran and 95.2 g (0.280 tool) of (3-methoxyphenyl)phosphonic acid diphenyl ester (material from dab) were placed under argon in a separate 1 l round flask and the solution was cooled to −78°. This solution was now allowed to flow via a steel canula within about 10 minutes into the above reaction mixture, whereby the temperature rose to about −78° and a transparent caramel-coloured solution resulted. This was stirred at −78° for a further 30 minutes.

A solution of 71.06 g (0.280mol) of iodine in 150 ml of dry tetrahydrofuran was prepared under argon in a separate 250 ml Schlenk tube and the solution was transferred via a steel canula into the dropping funnel of the reaction apparatus. The reaction mixture was now titrated within 15 minutes by the rapid dropwise addition of the iodine solution, whereby the reaction temperature rose to about −65°. After the dropwise addition of about 145 ml of the about 170 ml of iodine solution, when a red coloration of the reaction mixture remained, the addition was interrupted and the mixture was left to warm to 0°. Then, the reaction mixture was treated with 150 ml of a solution of 100 g of sodium thiosulphate pentahydrate in 200 ml of deionized water, stirred vigorously and subsequently treated with 100ml of sat. NaHCO₃ solution. The two-phase system was filtered in order to remove the precipitate formed and the phases were separated. The aqueous phase was re-extracted once with 250 ml of ethyl acetate and the combined organic phases, were washed with 250 ml of sat. NaCl solution, dried over MgSO₄ and evaporated. The residue was again taken up in 500 ml of ethyl acetate and the solution was washed three times with 250 ml of deionized water and with 250 ml of sat. NaCl solution, dried over MgSO₄, filtered and concentrated. The residue (118 g of yellow oil) was taken up in 170 ml of toluene and the solution was treated with 115 ml of hexane, whereby a white precipitate separated. This was removed by filtration and the filtrate was applied to a column of 450 g of silica gel. Byproducts were firstly eluted with 2 l of hexane/ethyl acetate 9:1 and 3 l of hexane/ethyl acetate 8:2. Subsequently, fractions containing the end product were eluted with 2 l of hexane/ethyl acetate 7:3. After evaporation and drying in a high vacuum (≈10 Pa) at 60° for 1 hour there were obtained 76.5 g of an orange oil. This consisted of 75 mol% of (2-iodo-3-methoxyphenyl)phosphonic acid diphenyl ester according to ¹H-NMR analysis.

The other ligands can be prepared in an analogous manner to the foregoing.

We claim:

1. A process for producing a isoprene derivative of the formula:

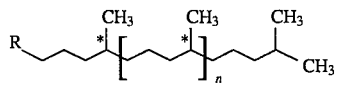

wherein R is:

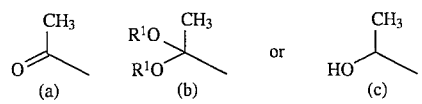

$R^1$ is lower alkyl or both $R^1$'s together are ethylene or propylene, n is 0, 1 or 2, and the asymmetric centres each individually can have the (R)- or (S)-configuration, comprising asymmetrically hydrogenating a compound in the (E)- or (Z)-form of the formula:

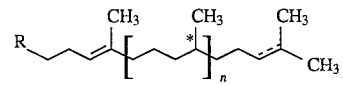

wherein R and n are as above, and the dotted line is an optional double bond, in the presence of a ruthenium complex of an optically active atropisomeric diphosphine ligand having the formula:

    III

    IV

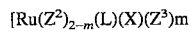    V wherein Z is $BF_4^\ominus$, $Cl_4^\ominus B(phenyl)_4^\ominus$ or $PF_6^\ominus$, $Z^1$ is halogen or the group $Y-COO^\ominus$ or $Y-SO_3^\ominus$, Y is lower alkyl, phenyl, halogenated lower alkyl or halogenated phenyl, $Z^2$ is halogen, X is benzene, hexamethylbenzene or p-cymene and m is 1 or 2, $Z^3$ is halogen, $BF_4^\ominus$, $Cl_4^\ominus$ or $B(phenyl)_4^\ominus$, and L is the optically active atropisomeric diphosphine ligand which is present in the (R)- or (S)-form and is of the formula:

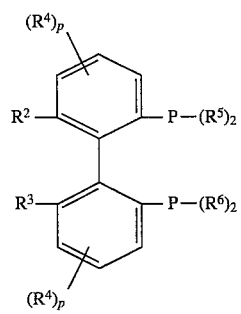    VI wherein $R^2$ and $R^3$ each independently are lower alkyl, lower alkoxy, hydroxy, or protected hydroxy or and together is $—O—CH_2—O—CH_2—O—$, $R^4$ is lower alkyl or lower alkoxy, p is 0, 1 or 2, and $R^5$ and $R^6$ each independently are aryl, a five-membered heteroaromatic group or, together with the phosphorous atom, a group of the formula:

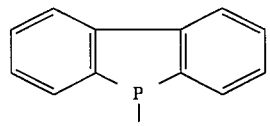

to obtain said isoprene derivative.

2. The process of claim 1, wherein the ruthenium complex is

    III.

3. The process of claim 2 wherein the compound of formula I is (R)- or (S)-6,10-dimethylundecan-2-one and the compound of formula II is (E)- or (Z)-6,10-dimethylundec-5-en-2-one.

4. The process of claim 2 wherein $R^5$ and $R^6$ are both phenyl.

5. The process of claim 4 wherein L is (6,6'-dimethoxybiphenyl-2,2'diyl) bis(diphenylphosphine).

6. The process of claim 4 wherein L is (6,6'-dimethoxybiphenyl-2,2'diyl)bis {bis-[3,5-di(trimethylsilyl)phenyl]phosphine}.

7. The process of claim 4 wherein L is (6,6'-dimethoxybiphenyl-2,2'-diyl) bis[bis-(3,4,5-trimethoxyphenyl)phosphine].

8. The process of claim 4 wherein L is (6,6'-dimethoxybiphenyl-2,2'-diyl) bis {bis-[p-(N,N-dimethylaminosulphamoyl)phenyl]phosphine }.

9. The process of claim 4 wherein L is (6-isopropoxy-6'-hydroxybiphenyl-2,2'-diyl) bis(diphenylphosphine).

10. The process of claim 4 wherein L is (6,6'-diisopropoxybiphenyl-2,2'diyl) bis(diphenylphosphine).

11. The process of claim 4 wherein L is (6,6'-dibenzyloxybiphenyl-2,2'diyl) bis(diphenylphosphine).

12. The process of claim 4 wherein L is (6,6'-dimethoxybiphenyl-2,2'-diyl) bis(di-4-biphenylylphosphine).

13. The process of claim 4 wherein L is (6,6'dimethoxybiphenyl-2,2'-diyl) bis {bis-[p-(N,N-dimethylamino)phenyl] phosphine }.

14. The process of claim 4 wherein L is (6,6'-dimethoxybiphenyl-2,2-diyl) bis[di-(p-methoxyphenyl)phosphine ].

15. The process of claim 4 wherein L is (4,4',5,5',6,6'-hexamethoxybiphenyl-2,2'-diyl) bis(diphenylphosphine).

16. The process of claim 4 wherein L is (5,7-dihydrodibenz[c,e]oxepin-1,11-diyl) bis(diphenylphosphine).

17. The process of claim 2 wherein L is (6,6'-dimethoxybiphenyl-2,2'-diyl) bis[di-p-tolylphosphine].

18. The process of claim 4 wherein $R^5$ and $R^6$ are both furyl.

19. The process of claims 18 wherein L is (6,6'-dimethoxybiphenyl-2,2'-diyl) bis(di-2-furylphosphine).

20. The process of claim 18 wherein L is (6,6'dimethoxybiphenyl-2,2'-diyl) bis(di-3- furylphosphine).

21. The process of claim 18 wherein L is (6,6'-methoxybiphenyl-2,2'diyl) -bis-[di-(2-benzo[b ]furanyl)phosphine ].

22. The process of claim 18 wherein L is (6,6'-dimethoxybiphenyl-2,2-diyl) bis[bis(5-methylfuran-2-yl)phosphine ].

23. The process of claim 2 wherein $R^5$ and $R^6$ are both thienyl.

24. The process of claim 23 wherein L is ((6,6'-dimethoxybiphenyl-2,2-diyl) bis(di-2-thienylphosphine).

25. The process of claim 23 wherein L is (6,6'-dimethylbiphenyl-2,2-diyl) bis(di-2-thienylphosphine).

26. The process of claim 2 wherein one of $R^5$ and $R^6$ is phenyl and the other is thienyl.

27. The process of claim 26 wherein L is P,P-diphenyl-P',P',-di-2-thienyl-(6,6'-dimethylbiphenyl-2,2'-diyl) diphosphine.

28. The process of claim 2 wherein $R^5$ and $R^6$ are both groups of the formula:

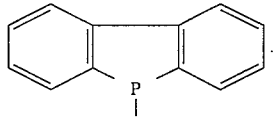

29. The process of claim 28 wherein L is 5,5'-(6,6'-dimethylbiphenyl-2,2-diyl) 5H-benzo[b]phosphindole.

30. The process of claim 1 wherein the ruthenium complex is $$Ru(Z^1)_2L \qquad \text{IV.}$$

31. The process of claim 30 wherein R5 and R6 are both furyl.

32. The process of claim 31 wherein L is (6,6'-dimethoxybiphenyl-2,2-diyl) bis(di-2-furylphosphine).

* * * * *

UNITED STATES PATENT AND TRADEMARK OFFICE
CERTIFICATE OF CORRECTION

PATENT NO. : 5,600,015
DATED : February 4, 1997
INVENTOR(S) : BROGER ET AL.

It is certified that error appears in the above-indentified patent and that said Letters Patent is hereby corrected as shown below:

Column 14:

Claim 1, lines 27 and 31, delete "$Cl_4$" and insert therefor -- $ClO_4$ --.

Claim 1, line 48, replace "or and together" with -- or $R^2$ and $R^3$ together --.

Column 15:

Claim 17, first line, replace "claim 2" with --claim 4--.

Claim 18, first line, replace "claim 4" with --claim 2--.

Signed and Sealed this

Twentieth Day of May, 1997

Attest:

BRUCE LEHMAN

*Attesting Officer*   *Commissioner of Patents and Trademarks*